United States Patent [19]

Burton et al.

[11] Patent Number: 5,217,962

[45] Date of Patent: Jun. 8, 1993

[54] METHOD AND COMPOSITION FOR TREATING PSORIASIS

[76] Inventors: Albert F. Burton, 297 Rodello Street, Comox, B. C., Canada, V9N 4Z9; David I. McLean, 855 West 10th Avenue, Vancouver, B. C., Canada, V5Z 1L7

[21] Appl. No.: 826,764

[22] Filed: Jan. 28, 1992

[51] Int. Cl.$^5$ .............................................. A61K 31/70
[52] U.S. Cl. ....................................... 514/62; 514/863
[58] Field of Search ................................. 514/62, 863

[56] References Cited

U.S. PATENT DOCUMENTS 3,697,652 10/1972 Rovati et al. .
4,006,224 2/1977 Prudden .
4,590,067 5/1986 Meisner .

FOREIGN PATENT DOCUMENTS

WO87/02244 4/1987 PCT Int'l Appl. .

OTHER PUBLICATIONS

Schloss, "Extraintestinal Manifestations", *Idiopathic Inflammatory Bowel Disease*, Thomson A. B. R. ed., M.O.M. Printers, Ottawa, 1982, Ch. 23.

Lawley et al., "Exzema, Psoriasis, Cutaneous Infections, Acne, and Other Common Skin Disorders", *Harrison's Principles of Internal Medicine*, 12th ed., Ch. 56, 1991.

Burton et al., "Decreased Incorporation of $^{14}$C--Glucosamine Relative to $^3$H-N-Acetyl Glucosamine in the Intestinal Mucosa of Patients with Inflammatory Bowel Disease", *Amer. Journal of Gastroenterology*, vol. 78, No. 1, pp. 19-22, 1983.

*Primary Examiner*—Leonard Schenkman
*Attorney, Agent, or Firm*—Barrigar & Oyen

[57] ABSTRACT

This invention pertains to the novel use of N-acetyl glucosamine as a cytoprotective agent for persons afflicted with psoriasis by restoring integrity and normal function of skin. A method of treating psoriasis in a human being comprising feeding the human being a therapeutic amount of N-acetyl glucosamine, or a pharmaceutically acceptable salt thereof, on a periodic basis.

5 Claims, No Drawings

METHOD AND COMPOSITION FOR TREATING PSORIASIS

FIELD OF THE INVENTION

This invention pertains to the novel use of N-acetyl glucosamine as a cytoprotective agent for persons afflicted with psoriasis by restoring integrity and normal function of skin.

BACKGROUND OF THE INVENTION

The skin is the largest organ in the human body and the cells which form the three skin layers are in a constant state of growth, with the outer layer of dead tissue being constantly shed. Replacement of cells from underlying layers is accomplished by cell division and maturation, the cells moving outward constantly at a rate that varies with age, sex, and other conditions.

An increased turnover of cells, where there is an increased rate of cell growth and cell death, is a common accompaniment of many conditions including injuries and disorders of various types. In the accompanying increased synthesis of all tissue components there is a strain placed upon the biosynthetic capacities of cells. A major component of the material which covers cells and occupies the spaces between them is glycosaminoglycans (GAG), which are by weight approximately half composed of amino sugars derived from N-acetyl glucosamine (NAG). In skin, about one-fifth of all the glucose utilized by the skin is destined for conversion to amino sugars.

A condition in which cell proliferation is increased up to ten times normal is psoriasis. This occurs in about 2 percent of the population (Harrison's Principles of Internal Medicine, 12th ed., Ch. 56, 1991), but with greater frequency in some groups (Idiopathic Inflammatory Bowel Disease, Thomson, A.B.R. ed., M.C.M. Printers, Ottawa, Ch. 23, 1982). Persons with inflammatory bowel disease have a higher incidence, about 15 percent. This group also has a higher incidence of joint disorders, about 25 percent. Both these conditions have been related to abnormalities in formation of glycosaminoglycans. Many patients with psoriasis have abnormal fingernails. Fingernails are composed mostly of chitin, which is a polymer of N-acetyl glucosamine (NAG), and thus fingernails are greater than 99 percent composed of NAG.

Several patents disclose amino sugars for treatment of disorders.

U.S. Pat. No. 4,590,067, May 20, 1986, Meisner, Peritain Ltd. discloses a composition for preventing and treating periodontal disease comprising bone meal, ascorbic acid, tyrosine and either glucosamine or cysteine. N-acetyl glucosamine is not disclosed.

French Pat. No. 2,473,887, Jul. 24, 1981, discloses the use of biochemical precursors of glucosamineglycans for the treatment of vascular disorders of functional or organic origin in which there is insufficient blood flow to the limbs, for asphyxic hypoxydotic symptoms, and in cosmetology, for skin defects caused by insufficient circulation to the skin. The precursors, which include N-acetylglucosamine, increase the elasticity of perivascular tissue, resulting in an increase in arterio-capillary blood flow, without having a vasodilating action.

U.S. Pat. No. 4,006,224, Feb. 1, 1977, J.F. Prudden, discloses the treatment of ulcerative colitis or regional enteritis in a mammal by administering D-glucosamine, or one of its salts. Equal or superior results to the conventional treatments of the two conditions are obtained. The dose is 20-300 mg/kg of D-glucosamine, HCl daily. In a clinical trial, a patient with Crohn's Disease that was not affected by ACTH or prednisone was given D-glucosamine, HCl subcutaneously. The symptoms stopped after several weeks of treatment.

WO A 702 244, N. Hendry, EP A 0178602, Peritain Ltd. and French Patent A 2016 182, Rotta Research Labratorium SpA, are of interest to this subject.

Hendry discloses a three-component preparation for tissue growth regulation comprising (a) at least one of N-acetyl-D-glucosamine or an oligomer thereof, or a deacylated derivative thereof, or a substituted product of these compounds; (b) at least one of biotin or an analog or derivative biotin, or biologically active residue thereof; and (c) a divalent metal cation together with a pharmaceutically acceptable anion.

Both Meisner and Hendry refer to amino sugars, including glucosamine and N-acetyl glucosamine. Their use is as one of a mixture of several other known nutrients, which have various effects on cell growth.

A key difference in the applicant's proposed use of NAG is this: It is proposed as a source of amino sugar for the synthesis of molecules such as glycoproteins and glycosaminoglycans, which are rich in NAG and the synthesis of which is stimulated by NAG.

NAG is formed from glucosamine and NAG is then directly converted into other amino sugars. NAG is thus a key substance, and in the applicant's work with intestinal tissue, it was found that the formation of NAG itself from glucosamine was the slow part of the process. This necessitates the use of NAG, specifically, and not a deacetylated form, or oligomer.

NAG, moreover, is more stable than glucosamine, is a neutral substance and is readily assimilated by tissues and utilized, whereas most oligomers are not.

The proposed use of NAG is unique and differs from existing art.

An article entitled "Decreased Incorporation of $^{14}$C-Glucosamine Relative to $^3$H-N-Acetyl Glucosamine in the Intestinal Mucosa of Patients with Inflammatory Bowel Disease", A.F. Burton and F.H. Anderson, vol. 78, No. 1, 1983, American Journal of Gastroenterology, discloses evidence that the synthesis of glycoproteins in intestinal mucosa of patients afflicted with inflammatory bowel disease is deficient in the diseased tissues of such patients. The article discusses possible reasons for the deficiency. However, no suggestions for alleviating the deficiency are made.

SUMMARY OF THE INVENTION

The novel feature of this invention is the use of an external source of N-acetyl glucosamine which is ingested to rectify a deficit which, while not necessarily affecting the basic cause of the disorder of psoriasis, can provide for the formation of essential tissue components whose deficiency is a major facet of this disease. The N-acetyl glucosamine is effective without being applied directly to the external site of the psoriasis.

The invention is directed to a method of treating psoriasis in a human being comprising feeding the human being a therapeutic amount of N-acetyl glucosamine on a regular basis.

The N-acetyl glucosamine can be fed to the human being on a daily basis. The dosage can be about 300 mg to about 10,000 mg of N-acetyl glucosamine per day, about 1,000 mg to about 6,000 mg of N-acetyl glucosamine per day, or about 500 mg of N-acetyl glucosamine per day. The N-acetyl glucosamine can be incorporated in a pharmaceutically acceptable carrier.

The invention is also directed to a composition useful for treating psoriasis in a human being comprising N-acetyl glucosamine and a pharmaceutically acceptable carrier. The N-acetyl glucosamine can present in the amount of about 1,000 mg to about 6,000 mg, or about 500 mg.

DETAILED DESCRIPTION OF THE PREFERRED EMBODIMENT

There are tissue defects in the digestive tract of human beings suffering food intolerance or food allergies. These defects can be corrected to enable the mucosa in the tract to form a necessary barrier to transmission of food allergens and to maintain normal function. The mucosa tissue structure is rich in amino sugars derived from N-acetyl glucosamine and we have discovered that the availability of N-acetyl glucosamine is critical to its synthesis.

We have also discovered that an external source of N-acetyl glucosamine is useful to ensure adequate synthesis of the mucosal barrier. Indeed, we have found that the use of N-acetyl glucosamine alone might be sufficient in itself to treat milder food allergy cases. In more severe cases, the amino sugar, N-acetyl glucosamine, or a pharmaceutically acceptable salt thereof, might be combined with elemental diets so that the removal of offending substances is accomplished, while at the same time, providing the new amino sugar material necessary to enable the human body to generate coherent mucosa tissue and maintain its defenses.

N-acetyl glucosamine (NAG) is an amino sugar, which is formed in all animal cells and is utilized for the synthesis of many cellular components. The biochemical process by which these components are made is similar in all cells although the end products differ depending upon the type of cell involved. Most of the end products are found outside the cells where they form sheaths which bind cells together, and are major structural components, as in the walls of blood vessels, and fill the spaces between cells, i.e. the interstitium. Amino sugars are found combined with other large molecules (macromolecules) of protein, lipid (fats) or other carbohydrates to form glycoproteins (GP), glycolipids (GL) and glycosaminoglycans (GAG). Glycoproteins have many functions, some circulate in the blood, others are anchored on the surface of cells, as are glycolipids. They can confer unique properties to the cell, for example, on the surface of red blood corpuscles there is a glycolipid which determines the blood groups A, B and 0. The sole difference between these groups is the presence of a single amino sugar. Such remarkable specificity indicates that there is a "language" in which amino sugars are the "letters" analogous to the genetic code, by which biological information is recorded and put into action.

Each cell makes its own amino sugars and the process, as in the case of most biochemical synthesis, is regulated by the availability of the first member of the sequence, which in this case is glucosamine. Glucosamine is formed from the pool of sugars derived from glucose, blood sugar, and is acetylated to form N-acetyl glucosamine (NAG). NAG is the immediate precursor for two other amino sugars, N-acetyl galactosamine and N-acetyl neuraminic (sialic) acid. These amino sugars constitute about half the total weight of the GAG found in human tissues (References 1-7).

In the synthesis of these molecules, the availability of the substrate, amino sugars, is critical to proper function. We have discovered that although the formation and utilization of amino sugars takes place in all human cells independently, nevertheless an external source of amino sugar is readily taken up by the cells and is utilized by them for incorporation into the macromolecules. An external source of amino sugar, we have found, can provide for an adequate amount of substrate to satisfy cell demands which otherwise might be greater than the cells can meet.

The interstitium is the space between the cells which contains the fibrous protein collagen ensheathed by glycosaminoglycan (GAG). The GAG absorbs very large quantities of water to form a gel-like material which resists compression thereby giving shape and firmness to the tissue. This material acts as a medium which regulates the passage of nutrients, etc., between the blood and the tissues, and also acts as a barrier, for example, to the spread of infection (Bert and Pearce).

Mucous membranes are covered by a microscopically thin glycoprotein rich in sialic acid called the glycocalyx. In the gastrointestinal tract (GI), this microscopically thin layer is the ultimate barrier between the underlying tissue and the corrosive digestive juices. When the layer is damaged, erosion and ulceration of the underlying tissue occurs. If the blood supply to the upper GI is arrested for about 5 minutes, for example, it has been found that all synthetic processes cease, including formation of the glycocalyx, and an ulcer can be seen forming within an hour. This illustrates the dynamic nature of the biological processes in the human body. There are several hundred grams of amino sugar in the various tissue components of the body but the average life of a given molecule is only 3 days or so. There is thus a constant turnover of all molecules in the body, even in tissues such as bone, and a constant supply of substrates for synthesis is therefore required.

An important and novel feature of the present invention is that increased demands caused by injury such as food allergen injury can be placed upon cells which might strain their resources, and in this situation, an external supply of amino sugars is beneficial. In the gastrointestinal tract (GI), the rate of synthesis of the glycocalyx had been considered to be adequate in persons afflicted with Inflammatory Bowel Disease (IBD). However, in such persons, as in many situations where there is disease or injury, the turnover of cells is increased, perhaps as much as threefold. This creates a demand that is beyond what is considered normal. We have found that the incorporation of NAG into the intestinal mucosal tissue is three times greater in persons afflicted with IBD than in those who are not afflicted.

We have also found that in human placenta near term, the formation of glycosaminoglycan (GAG) is stimulated strongly by the steroid 17 α-hydroxyprogesterone (Burton et al.) which appears to function by increasing the synthesis of amino sugars. We have discovered that the same stimulation can be achieved merely by providing the appropriate amino sugars.

Others have shown that in chondrocytes, the cells which form cartilage, the presence of corticosteroids inhibits the formation of GAG. Supplying amino sugars largely overcame this inhibition (Fassbender).

In a recent publication, the question of intestinal permeability in persons with Crohn's Disease, a form of IBD, was reviewed (Olaison et al.). It was found that these persons have greater than normal permeability of the GI tract which leads to the absorption into the bloodstream of substances normally excluded. This includes the substances which cause food sensitivities or food allergies. The condition is attributed to a defect in the mucosal barrier, the glycocalyx, and the intercellular cement composed of GG. Even unaffected relatives of these patients have been found to have increased permeability (Hollander et al.) which supports the concept that some individuals have a genetic or constitutional defect which sets the stage for a spectrum of disorders ranging from mild to serious food intolerance to severe inflammatory lesions.

Various agents inhibit the formation of the mucosal barrier including ethanol, aspirin and other antiinflammatory agents. Erosion and bleeding of the GI tract is a major side-effect of such drugs. An agent, proglumide, which protects against ulcer formation has been shown to stimulate the incorporation of NAG into mucosal glycocalyx and this is considered the reason for its effectiveness (Umetsu).

Inflammation is a common accompaniment of many forms of injury and is part of the body's defence and repair mechanism. Often, however, the inciting agent is such that the inflammation serves no protective purpose and in fact results in tissue damage causing pain and disability, as in arthritis.

There are, therefore, many situations where an external source of amino sugar can be beneficial. We have discovered that a good choice is N-acetyl glucosamine (NAG) which is a neutral compound, is stable, is very soluble, is tasteless, and is readily absorbed from the digestive tract. It circulates in the blood with a half-life of about 4 hours and very little is excreted since it is a "committed metabolite" utilized exclusively for the synthesis of GP, GL, GAG in tissue components. An external supply, we have found, is readily taken up and utilized by the human body and therefore has the potential to be of benefit in many situations where the synthetic processes are less than adequate to meet demands. NAG alone is capable of efficient utilization for these processes when taken by mouth.

EXAMPLE 1

Case History—G.O.S.O.

G.O.S.O., male, 55, for about three years, had been suffering from periodic inflammation and mucousal drainage of the lower bowel area, a condition sometimes known as irritable bowel syndrome. For about the same time, G.O.S.O. experienced a problem with psoriasis on each side of his nose. G.O.S.O. consulted his physician to investigate the bowel complaint. The physician conducted an examination and concluded that G.O.S.O. should undergo a barium enema/X-ray examination.

G.O.S.O. attended the radiologist's office after undergoing the prescribed two day liquid diet and the barium enema X-ray testing procedure was conducted. The results of the examination indicated that G.O.S.O. had an inflamed bowel condition known medically as diverticulitis/diverticulosis, which is a condition common for persons who are fifty or more years of age. The physician said that the initial treatment that is usually prescribed for a person afflicted with diverticulitis is a daily supplement of 4 tablespoons of wheat bran. If the supplement of wheat bran did not bring about an improvement, then antibiotics would be prescribed.

G.O.S.O. began to include four tablespoons of wheat bran in his morning breakfast cereal, but over the next two weeks, did not notice any significant improvement in his diverticulitis condition.

G.O.S.O. then commenced to take four 500 mg capsules of N-acetyl glucosamine per day. Within three days of commencing the treatment, G.O.S.O. noticed a very obvious significant reduction in the mucous emission rate from his lower bowel area. G.O.S.O. also noticed that the irritation around his rectum cleared up in a matter of days.

G.O.S.O. continued a daily dosage rate of 2 g of N-acetyl glucosamine for fifteen days. However, G.O.S.O. did not have an opportunity to purchase a replacement of 500 mg. N-acetyl glucosamine capsules. Within three days, G.O.S.O. noticed that there was a recurrence of the mucous discharge from his lower bowel area. Prior to that, the mucous discharge had stopped for about twelve days and there was a dramatic improvement in his inflamed bowel condition.

G.O.S.O. then purchased two 60 capsule containers of 500 mg N-acetyl glucosamine capsules and commenced treatment again at a 2 g per day NAG dosage rate. As before, after about three days of treatment, G.O.S.O. noticed a strong reduction in the anal mucous discharge rate. The problem was cleared up in about five days after recommencing treatment with N-acetyl glucosamine. G.O.S.O. continued taking 2 g of N-acetyl glucosamine per day for six weeks. During that period of time, the mucous discharge due to an inflamed bowel condition was completely terminated.

The psoriasis condition on each side of the lower part of his nose that G.O.S.O. had experienced for about three years, was treated with cortisone steroid antifungal creams. This treatment had been largely ineffective. After daily ingestion of 2 g of N-acetyl glucosamine for treatment of the diverticulutis, G.O.S.O. noticed that the psoriasis condition cleared up. There has been no return of the psoriasis condition.

EXAMPLE 2

Case History—J.F.

Over a period of two or more years, J.F. developed a bowel disorder that caused periods of considerable pain and discomfort. She also developed a persistent psoriasis condition, which did not succumb to treatment with standard psoriasis treatment creams. In September of 1987, J.F. underwent an operation for an unrelated problem and at that time the attendant physician noticed that J.F. had an inflamed bowel. That physician and others that J.F. consulted thereafter offered no particular treatment apart from a possible operation in the event that the condition, which they diagnosed as diverticulitis, became severe.

In late September, 1987, J.F. began taking a daily dose of N-acetyl glucosamine in an amount approximating one teaspoonful (2 g) per day. J.F. dissolved this in fruit juice and sipped the juice at frequent intervals over the daytime. J.F.'s intestinal condition improved a great deal and she had no further serious attacks of diverticulitis. During this time, J.F. underwent a series of X-rays and sigmoidoscope examinations which confirmed that J.F. did indeed have diverticulitis.

By the early part of December, 1987, J.F. was feeling so much better that she decided to reduce the amount of NAG she was consuming daily. J.F. did this gradually until she was down to about ¼ tsp. (0.5 g) per day. In late December, 1987, J.F. had a mild recurrence of the intestinal symptoms that she had experienced previously. J.F. returned to a larger daily dose of NAG, about 3/4 tsp. (1.5 g) per day, and the symptoms disappeared. In late Jan. 1988, J.F. and her husband went on holidays for two weeks during which time her consumption of NAG became somewhat irregular. Shortly before returning home, J.F. had another recurrence of the bowel disorder - again a mild one, but the symptoms subsided about 48 hours after resuming a steady daily intake of NAG. Since then J.F. has maintained a daily dose of NAG amounting to about ¾ tsp. which she takes in three portions, morning, noon and at night before bed. She has been completely symptom-free since then. Her psoriasis condition has also cleared up and is in remission.

When J.F. reduces her daily NAG dosage to less than ½ tsp. (about 1.0 g) per day, she finds that adverse intestinal and other symptoms recur, including her psoriasis condition. However, consistent treatment with NAG minimizes or eliminates the symptoms.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

1. Balazs, E.A., Jeanloz, R.W.: The Amino Sugars. Academic Press, New York, 1965, vol. IIA.

2. Heinegard, D., Paulsson, M.: Extracellular Matrix Biochemistry. Piez, K.A., Reddi, A.H. eds., Elsevier, New York, 1984.

3. Varma, R., Varma, R.S.: Mucopolysaccharides—Glycosaminoglycans—of Body Fluids in Health and Disease. W. de Gruyter, New York, 1983.

4. Schachter, H.: Biosynthetic controls that determine the branching and microheterogeneity of protein-bound oligosaccharides. Biochemistry and Cell Biology 1986, 64: 163-181.

5. Lukie, B.E., Forstner, G.G.: Synthesis of intestinal glycoprotein. Incorporation of $^{14}$C-glucosamine in vitro. Biochimica et Biophysica Acta 1972, 261: 353-364.

6. Bert, J.L., Pearce, R.H.: The Interstitium and Microvascular Exchange. Handbook of Physiology—The Cardiovascular System IV, 1984, 521-547.

7. Zubay, G.: Biochemistry 2nd ed. MacMillan Publishing Co., New York, 1988, 663.

8. Burton, A.F., Anderson, F.H.: Decreased incorporation of $^{14}$C-glucosamine relative to $^3$H-N-acetyl glucosamine in the intestinal mucosa of patients with inflammatory bowel disease. American Journal of Gastroenterology 1983, 78: 19-22.

9. Burton, A.f., Lockhart, F., Bosnjak, S., Yong, S.: Stimulation by 17-alpha-hydroxyprogesterone of glycoprotein and glycosoaminoglycan synthesis in human placenta in vitro. Biology of the Neonate 1989, 55: 151-155.

10. Fassbender, H.G.: Role of chondrocytes in the development of osteoarthritis. American Journal of Medicine 1987, 83 (supp. 5A) 17-24.

11. Olaison, G., Sjodahl, R., Tagesson, C.: Abnormal Intestinal Permeability in Crohn's Disease. Scandinavian Journal of Gastroenterology, 1990, 25: 321-328.

12. Hollander, D. et al.: Increased intestinal permeability in patients with Crohn's Disease and their relatives. Annals of Internal Medicine 1986, 105: 883-885.

13. Umetsu, T. et al.: Effect of proglumide on glycoprotein synthesis in aspirin-induced gastric erosions in rats. European Journal of Pharmacology 1980, 69: 69-77.

We claim:

1. A method of treating psoriasis in a human being suffering from psoriasis comprising feeding the human being suffering from psoriasis a therapeutic amount of N-acetyl glucosamine on a daily basis until the psoriasis condition is alleviated.

2. A method according to claim 1 wherein the human being is fed about 300 mg to about 10,000 mg of N-acetyl glucoasmine per day.

3. A method according to claim 1 wherein the human being is fed about 1,000 mg to about 6,000 mg of N-acetyl glucosamine per day.

4. A method according to claim 1 wherein the human being is fed about 500 mg of N-acetyl glucosamine per day.

5. A method according to claim 2 wherein the N-acetyl glucosamine is incorporated in a pharmaceutically acceptable carrier.

* * * * *